United States Patent
Ronchi et al.

(10) Patent No.: US 10,835,610 B2
(45) Date of Patent: Nov. 17, 2020

(54) PHARMACEUTICAL OR COSMETIC COMPOSITIONS COMPRISING A POLYMER AND AN ABSORPTION PROMOTER FOR CONTROLLED RELEASE OF ACTIVE INGREDIENTS

(71) Applicant: EMENEM s.r.l., Milan (IT)

(72) Inventors: Celestino Ronchi, Milan (IT); Federica Ronchi, Milan (IT)

(73) Assignee: EMENEM S.R.L., Milan (IT)

( * ) Notice: Subject to any disclaimer, the term of this patent is extended or adjusted under 35 U.S.C. 154(b) by 192 days.

(21) Appl. No.: 15/437,802

(22) Filed: Feb. 21, 2017

(65) Prior Publication Data

US 2017/0239357 A1 Aug. 24, 2017

(30) Foreign Application Priority Data

Feb. 24, 2016 (IT) .................. 102016000019260

(51) Int. Cl.
| | |
|---|---|
| *A61K 47/34* | (2017.01) |
| *A61K 47/32* | (2006.01) |
| *A61K 31/728* | (2006.01) |
| *A61K 47/28* | (2006.01) |
| *A61K 9/06* | (2006.01) |
| *A61K 31/522* | (2006.01) |
| *A61Q 19/00* | (2006.01) |
| *D06M 15/333* | (2006.01) |
| *A61K 8/99* | (2017.01) |
| *A61K 8/02* | (2006.01) |
| *D06M 16/00* | (2006.01) |
| *A61K 8/91* | (2006.01) |
| *D06M 15/00* | (2006.01) |
| *D06M 13/00* | (2006.01) |
| *D06M 15/53* | (2006.01) |
| *D06M 15/356* | (2006.01) |
| *A61K 8/04* | (2006.01) |
| *A61K 8/49* | (2006.01) |
| *A61K 8/55* | (2006.01) |
| *A61K 8/64* | (2006.01) |
| *A61K 8/73* | (2006.01) |
| *A61K 8/86* | (2006.01) |
| *A61K 9/00* | (2006.01) |
| *A61K 9/08* | (2006.01) |
| *A61K 9/70* | (2006.01) |
| *A61K 31/196* | (2006.01) |
| *A61K 47/24* | (2006.01) |

(52) U.S. Cl.
CPC ............ *A61K 47/34* (2013.01); *A61K 8/0208* (2013.01); *A61K 8/0216* (2013.01); *A61K 8/0233* (2013.01); *A61K 8/042* (2013.01); *A61K 8/4953* (2013.01); *A61K 8/553* (2013.01); *A61K 8/64* (2013.01); *A61K 8/735* (2013.01); *A61K 8/86* (2013.01); *A61K 8/91* (2013.01); *A61K 8/99* (2013.01); *A61K 9/0014* (2013.01); *A61K 9/06* (2013.01); *A61K 9/08* (2013.01); *A61K 9/7007* (2013.01); *A61K 31/196* (2013.01); *A61K 31/522* (2013.01); *A61K 31/728* (2013.01); *A61K 47/24* (2013.01); *A61K 47/28* (2013.01); *A61K 47/32* (2013.01); *A61Q 19/00* (2013.01); *A61Q 19/007* (2013.01); *D06M 13/00* (2013.01); *D06M 15/00* (2013.01); *D06M 15/333* (2013.01); *D06M 15/3562* (2013.01); *D06M 15/53* (2013.01); *D06M 16/00* (2013.01); *A61K 2800/5422* (2013.01)

(58) Field of Classification Search
CPC ...... A61K 9/0014; A61K 9/08; A61K 8/0208; A61Q 19/00; A61Q 19/007
See application file for complete search history.

(56) References Cited

U.S. PATENT DOCUMENTS

| | | | | |
|---|---|---|---|---|
| 5,565,213 | A * | 10/1996 | Nakamori | A61K 9/127 424/450 |
| 5,854,226 | A * | 12/1998 | Penkler | A61K 31/192 514/58 |
| 2007/0081963 | A1* | 4/2007 | Oh | A61K 8/14 424/70.14 |
| 2007/0082042 | A1* | 4/2007 | Park | A61K 9/0014 424/450 |
| 2014/0094526 | A1* | 4/2014 | Marathi | A61K 31/192 514/784 |
| 2014/0134246 | A1* | 5/2014 | Venkatesh | A61K 31/4174 424/465 |
| 2015/0209343 | A1* | 7/2015 | Lu | A61K 31/4436 424/502 |
| 2016/0058717 | A1* | 3/2016 | Page | A61K 45/06 514/632 |

OTHER PUBLICATIONS

Bhuptani et al. ("Soluplus Based Polymeric Micelles and Mixed Micelles of Lornoxicam: Design, Characterization and In vivo Efficacy Studies in Rats", Indian Journal of Pharmaceutical Education and Research, 50(2), Apr. 2016, 277-286,.*

Bhuptani et al. journal homepage and abstract ("Soluplus Based Polymeric Micelles and Mixed Micelles of Lornoxicam: Design, Characterization and In vivo Efficacy Studies in Rats", Indian Journal of Pharmaceutical Education and Research, 50(2), Apr. 2016, 2 pages, Published on Dec. 2015.*

* cited by examiner

*Primary Examiner* — Kortney L. Klinkel

(74) *Attorney, Agent, or Firm* — Nixon & Vanderhye

(57) ABSTRACT

Disclosed is a pharmaceutical or cosmetic composition or medical device for topical use including: a) a cosmetically or pharmaceutically active substance; b) a polyvinylcaprolactam/polyvinyl acetate/polyethylene glycol copolymer; and c) a phospholipid. Also disclosed is a method for treatment incorporating such a composition.

5 Claims, 1 Drawing Sheet

PHARMACEUTICAL OR COSMETIC COMPOSITIONS COMPRISING A POLYMER AND AN ABSORPTION PROMOTER FOR CONTROLLED RELEASE OF ACTIVE INGREDIENTS

FIELD OF INVENTION

The present invention relates to pharmaceutical or cosmetic compositions or medical devices for topical use containing a cosmetically or pharmaceutically active substance, a polyvinylcaprolactam/polyvinyl acetate/polyethylene glycol copolymer and a phospholipid. The present invention also relates to the use of said compositions in the treatment of the skin or mucosa.

TECHNICAL BACKGROUND

Topical administration of active ingredients is widely used in the pharmaceutical and cosmetic field. A topically administered active ingredient can act locally in the area of application or systemically by entering the bloodstream.

Human skin, in particular the outer layer or stratum corneum, provides an effective barrier against the penetration of microbial pathogens and toxic chemicals. However, this barrier effect makes the topical application of active ingredients difficult, because many, if not most of the active ingredients applied to the skin of a patient suffering from a skin disease are unable to penetrate the layers of the skin most vital for the exercise of its activities.

In the case of topical systemic administration, the active ingredient must penetrate the skin and be absorbed into the bloodstream. It is therefore essential for the active ingredient to have sufficient permeability to pass through the skin, and sufficient solubility in water for systemic absorption to take place.

Numerous active ingredients used in the pharmaceutical and cosmetic industries possess low solubility in water and/or permeability.

To increase the permeability of the active ingredients, substances that promote absorption (penetration enhancers) are commonly used, including phospholipids, which are known for their high skin tolerability, as reported in the following scientific articles:

D. D. Verma et al. (Synergistic penetration enhancement effect of ethanol and phospholipids on the topical delivery of cyclosporin A—Journal of controlled release, 2004—Elsevier)

R. Kumar et al. (Lecithin organogels as a potential phospholipid-structured system for topical drug delivery: a review—AAPS pharmscitech, 2005—Springer)

P. Balakrishnan et al. (Formulation and in vitro assessment of minoxidil niosomes for enhanced skin delivery—International journal of Pharmaceutics, Volume 377, Issues 1-2, 30 Jul. 2009, Pages 1-8—Elsevier)

A. Bhatia et al. (Tamoxifen in topical liposomes: development, characterization and in-vitro evaluation—J Pharm Sci, 2004)

R. Aggarwal et al. (Miconazole nitrate-loaded topical liposomes—Pharm Tech, 2002)

It has now been discovered that the addition of a polyvinylcaprolactam/polyvinyl acetate/polyethylene glycol copolymer to the combination of an active ingredient with phospholipids makes it possible to obtain aqueous solutions of active ingredients with a high level of skin absorption.

Soluplus® is a novel type of polymer marketed by the company BASF as a polymeric solubilising agent with an amphiphilic chemical structure. This characteristic gives it good solubility in water and in various organic solvents.

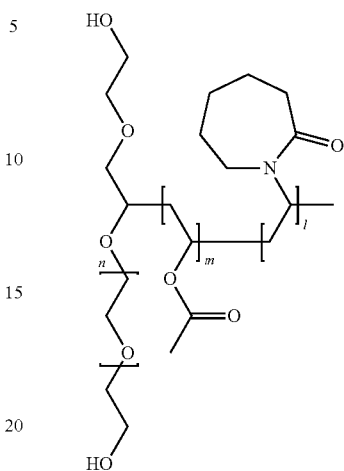

Chemically, Soluplus® is a polyvinylcaprolactam/polyvinyl acetate/polyethylene glycol graft copolymer, which is mainly used in solid oral formulations in combination with poorly soluble active ingredients. Its average molecular weight determined by gel permeation is between 90,000 and 140,000 g/mol.

Solid dispersions, active ingredient/Soluplus®, can be obtained in various ways, including extrusion or the spray-drying technique. The latter process involves preparing a solution of polymer and active ingredient in a preferably organic solvent (ethanol, acetone, etc). The solution is then sprayed in a countercurrent of air or nitrogen at high temperatures, close to the evaporation temperature of the solvent, to obtain a PA/polymer powder. This technique has demonstrated that it is possible to increase the solubility of poorly water-soluble active ingredients such as atorvastatin, albendazole, megestrol acetate, phenobarbital, itraconazole and indomethacin (D. Smithey et al Evaluation of the Polymer Soluplus® for Spray-Dried Dispersions of Poorly Soluble Compounds http://www.pharmaingredients.basf-.com/Documents/ENP/Poster/EN/Evaluation %20of %20the %20Polymer %20Soluplus.pdf).

In practice, Soluplus® physically interacts with the active principle by amorphising it, thus leading to an improvement in its solubility. The amphiphilic characteristics of Soluplus® also increase the wettability of the novel AP/Soluplus preparation.

This application has been extensively illustrated and scientifically discussed; in a recent article Alshahrani S. et al. (Stability-enhanced Hot-melt Extruded Amorphous Solid Dispersions via Combinations of Soluplus® and HPMCAS-HF. AAPS PharmSciTech. 2015 August; 16(4):824-34) described the use of Soluplus® in combination with HPM-CAS-HF (hydroxypropyl methylcellulose acetate succinate) in the manufacture of extrusions containing carbamazepine. The authors demonstrated that Soluplus®, either alone or in combination with other polymers, increases the dissolution rate of carbamazepine, improving its physicochemical stability after storage at 40° C./75% RH for 12 months.

WO 2011/028495 describes edible films for oral administration of active ingredients based on phenol extracts containing "edible and/or bioerodable" excipients, surfactants and oral absorption promoters. Soluplus® is reported in a long list of excipients. The oral absorption promoter is selected from fatty acids, glycerol and pegylated esters of fatty acids, phospholipids, polyethylene glycol ether, and combinations thereof.

Soluplus® has been extensively used to improve the solubility of active ingredients for oral use, but has been used with little success to carry active ingredients for mucosal or transcutaneous administration.

The use of Soluplus® for this route is limited by the glass transition temperature and tensile strength characteristics of the polymer. If used in a film it is stiff, inelastic, and difficult to use in topical formulations.

It is known from the literature that the addition of increasing concentrations of plasticisers improves the elongation characteristics of film containing Soluplus®, thus making the film suitable for topical application. In a recent article, Lim et al. tested various plasticisers in combination with Soluplus® polyethylene glycol 6 (PEG-6), triethyl citrate (TEC), propylene glycol (PPG) and glycerin (GLY), demonstrating that of all the plasticisers tested, PEG-6 modifies the mechanical properties of the film most efficiently (*Plasticizer Effects on Physical—Mechanical Properties of Solvent Cast Soluplus® Films*. AAPS PharmSciTech, Vol. 14, No. 3, September 2013).

However, Soluplus® also exhibited a limited ability to promote skin absorption.

M. Clough et al. (*Assessment of transdermal penetration enhancement by topical pharmaceutical excipients using skin PAMPA Method/AAPS Annual Meeting*, San Antonio, 2013) report that Soluplus® exhibits a high ability to solubilise active ingredients such as ibuprofen sodium salt, but considerably reduces its penetration. This last characteristic is attributed to the tendency of said polymer to complex, create aggregations or form micelles with the active ingredient.

DESCRIPTION OF THE INVENTION

Figure 1:
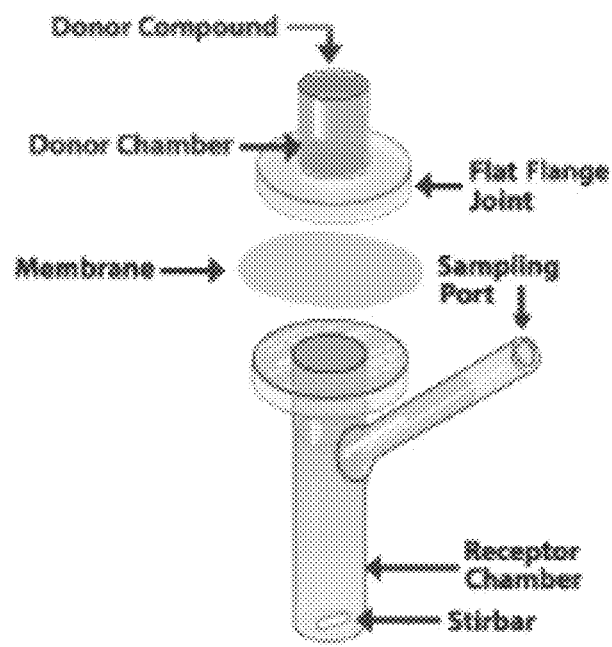
FIG. 1 is the schematic representation of the Franz cells used in the Permeation Test reported in Example 5 consisting of a receptor chamber and a donor compartment.

The Object of the present invention is a pharmaceutical or cosmetic composition or medical device for topical use comprising:
 a) a cosmetically or pharmaceutically active substance;
 b) a polyvinylcaprolactam/polyvinyl acetate/polyethylene glycol copolymer;
 c) a phospholipid.

The polyvinylcaprolactam/polyvinyl acetate/polyethylene glycol copolymer is preferably Soluplus®, made by BASF.

The phospholipid used in the composition according to the present invention is preferably selected from the group consisting of phosphatidylcholine and hydrogenated phosphatidylcholines with different degrees of purity, ranging from 50% to 90% purity.

In particular the phospholipid is hydrogenated phosphatidylcholine such as Phospholipon 80H, manufactured and marketed by the company Lipoid GmbH FrigenstraBe 4, 67065 Ludwigshafen am Rhein, Germany.

The weight ratio between the copolymer (polyvinylcaprolactam/polyvinyl acetate/polyethylene glycol) and the phospholipid ranges from 1:1 to 1:1000, preferably from 100:10 to 100:1.

The pharmaceutically and/or cosmetically active substance used in the composition for topical use according to the invention is preferably selected from the group consisting of antarcticine, polyglutamic acid, menthol/menthyl lactate, vanillyl butyl ester, escin, hyaluronic acid sodium salt, silver sulfadiazine, troxerutin and diclofenac sodium.

The active substance and the polymer are preferably solubilised in the preparation, and the absorption promoter is present in microdispersed form.

The composition according to the invention can be formulated as:
 a) solution to be applied directly to the skin
 b) solution to be sprayed directly onto the skin
 c) solution to be sprayed onto a medium (fabric) which, after evaporation of the solvent, is applied to the skin
 d) monolamellar film to be applied to the skin
 e) multilamellar (e.g. two-layer) film to be applied to the skin.

The compositions for topical use according to the present invention can be used in the treatment of diseases or lesions of the skin and/or mucosa, or for cosmetic treatment of the skin.

As regards liquid preparations, Soluplus has been used at concentrations ranging between 0.5% and 20% w/w.

The solvents preferably used are: purified water and/or water/ethanol mixtures on the basis of 100% water, or aqueous solutions with an alcohol content ranging between 5% and 30% weight/weight.

Technological adjuvants such as plasticisers, e.g. propylene glycol, glycerol, PEG-3, PEG 400 and PEG 3500, can also be used, at weight/weight concentrations ranging between 0.1% and 45%, preferably 20-30%.

In the case of films for topical use, the same substances, such as Soluplus, Phospholipon 80H and plasticisers, are used in the following ratios:
 Soluplus: Phospholipon 80H from 1:1 to 1:1000, preferably from 100:5 to 100:0.1, by weight.
 Soluplus: Plasticiser ranging between 1:0.05 and 1:0.4.

EXAMPLES

Example No. 1—Topical Cosmetic Film Based on Antarcticine

| Substance | % by weight | Quantity for 1 kg of solution | % content by weight of dry matter in the solution | % composition of film |
|---|---|---|---|---|
| Antarcticine solution with 25% dry matter | 3.00 | 30.00 g (equal to 7.5% dry matter) | 0.75% | 5.00 |
| Phospholipon 80H | 1.00 | 10.00 g | 1.00% | 6.67 |
| Propylene glycol | 4.00 | 40.00 g | 4.00% | 26.67 |
| Soluplus ® | 10.00 | 925.00 | 9.25% | 61.66 |
| Purified water | q.s. to 100% | 820.00 g | = | = |

Preparation Method:
Preparation of Solution:
Step #1: The required quantity of deionised water was introduced into a 2-litre glass beaker and weighed. The beaker was placed on a hotplate fitted with electromagnetic stirrer, and the water temperature was increased to 80° C.

Step #2: The Phospholipon 80 H was added to the water of step #1 and dispersed, maintaining the dispersion under stirring for about 30 minutes at the temperature of 80° C., until a complete microdispersion without lumps was obtained.

Step #3: The microdispersion of step #2 was cooled to room temperature, and the Soluplus® was then added under vigorous stirring. Stirring was maintained for at least 3 hours, until the Soluplus had completely dissolved. The antarcticine and propylene glycol were then added.

Step #4: The resulting solution was then filtered through an 8.0 micron filter membrane.

Step #5: The solution was then stored in a glass bottle with a usable capacity of 1 litre.

Film Preparation:

The film is prepared by spreading the solution on glass containers positioned perfectly horizontally on a surface and then placed in a thermostatic stove until a film is obtained by complete evaporation of the solvent.

Preparation of a Topical Film with 10 mg of Film/Cm$^2$:

A glass dish with an area of 56.7 cm$^2$ was prepared, and 3.78 g of the solution resulting from step #5 was weighed in it.

The dish thus filled was placed in a thermostatic stove under vacuum at the temperature of 30° C. for 8 hours.

The dish containing the film was then removed and left to cool at room temperature.

The resulting film was collected and placed in an aluminium/polythene sachet. The sachet was then heat-sealed.

Preparation of Topical Film with 20 mg of Film/Cm$^2$:

glass dish with an area of 56.7 cm$^2$ was prepared, and 7.56 g of the solution resulting from step #5 was weighed in it.

The dish thus filled was placed in a thermostatic stove under vacuum at the temperature of 30° C. for 8 hours.

The dish containing the film was then removed and left to cool at room temperature.

The resulting film was collected and placed in an aluminium/polythene sachet. The sachet was then heat-sealed.

Example No. 2—Topical Gel for Cosmetic Use Based on Hyaluronic Acid

| Substance | % by weight | Quantity for 1 kg of solution |
|---|---|---|
| Hyaluronic acid with a molecular weight of 1 million daltons | 0.10 | 1.00 g |
| Phospholipon 80H | 0.10 | 1.00 g |
| Propylene glycol | 3.00 | 30.00 g |
| Soluplus ® | 20.00 | 200.00 |
| Purified water | q.s. to 100% | 768.00 g |

Preparation Method:
Preparation of Solution:

Step #1: The required quantity of deionised water was introduced into a 2-litre glass beaker and weighed. The beaker was placed on a hotplate fitted with electromagnetic stirrer, and the water temperature was increased to 80° C.

Step #2: The Phospholipon 80 H was added to the water of step #1 and dispersed, maintaining the dispersion under stirring for about 30 minutes at the temperature of 80° C., until a complete microdispersion without lumps was obtained.

Step #3: The microdispersion of step #2 was cooled to room temperature, and the Soluplus® was then added under vigorous stirring. Stirring was maintained for at least 3 hours, until the Soluplus had completely dissolved. The hyaluronic acid and propylene glycol were then added, and stirring was maintained for a further 3 hours.

Step #4: The resulting solution was then filtered through an 8.0 micron filter membrane.

Packaging: The resulting gel was used to fill bottles fitted with a dispenser pump, which were then sealed.

Example No. 3—Caffeine-Based Cosmetic Solution for Spraying onto Undergarments

| Substance | % by weight | Quantity for 1 kg of solution |
|---|---|---|
| Caffeine | 0.50 | 5.00 g |
| Phospholipon 80H | 1.50 | 15.00 g |
| Soluplus ® | 0.10 | 1.00 g |
| Denatured ethanol | 30.00 | 300.00 |
| Purified water | q.s. to 100% | 679.00 g |

Preparation Method:
Preparation of Solution:

Step #1: The required quantity of deionised water was introduced into a 2-litre glass beaker and weighed. The beaker was placed on a hotplate fitted with electromagnetic stirrer, and the water temperature was increased to 80° C.

Step #2: The Phospholipon 80 H was added to the water of step #1 and dispersed, maintaining the dispersion under stirring for about 30 minutes at the temperature of 80° C., until a complete microdispersion without lumps was obtained.

Step #3: The microdispersion of step #2 was cooled to room temperature, and the Soluplus® was then added under vigorous stirring. Stirring was maintained for at least 3 hours, until the Soluplus had completely dissolved. The caffeine and denaturated ethanol were then added, and stirring was maintained for about 1 hour.

Step #4: The resulting solution was then filtered through an 8.0 micron filter membrane.

Packaging: The resulting solution was then used to fill bottles fitted with a spray pump.

Example No. 4—Topical Film Based on Diclofenac Sodium

| Substance | % by weight | Quantity for 1 kg of solution | % content by weight of dry matter in the solution | % composition of film |
|---|---|---|---|---|
| Diclofenac sodium | 1.00 | 10.00 g | 1.00% | 3.846 |
| Phospholipon 80H | 1.00 | 10.00 g | 1.00% | 3.846 |
| Propylene glycol | 4.00 | 40.00 g | 4.00% | 15.384 |
| Soluplus ® | 20.00 | 200.00 g | 20.00% | 76.924 |
| Purified water | q.s. to 100% | 740.00 g | = | = |

Preparation Method:
Preparation of Solution:
Step #1: The required quantity of deionised water was introduced into a 2-litre glass beaker and weighed. The beaker was placed on a hotplate fitted with electromagnetic stirrer, and the water temperature was increased to 80° C.

Step #2: The Phospholipon 80 H was added to the water of step #1 and dispersed, maintaining the dispersion under stirring for about 30 minutes at the temperature of 80° C., until a complete microdispersion without lumps was obtained.

Step #3: The microdispersion of step #2 was cooled to room temperature, and the Soluplus® was then added under vigorous stirring. Stirring was maintained for at least 3 hours, until the Soluplus had completely dissolved. The diclofenac sodium and propylene glycol were then added, and stirring was maintained for about 30 minutes.

Step #4: The resulting solution was then filtered through an 8.0 micron filter membrane.

Step #5: The solution was then stored in a glass bottle with a usable capacity of 1 litre.

Preparation of Film:
Preparation of Topical Film with 10 mg of Film/Cm$^2$:
The film is prepared by spreading the solution on glass containers positioned perfectly horizontally on a surface and then placed in a thermostatic stove until a film is obtained by complete evaporation of the solvent.

Preparation of a Topical Film with 10 mg of Film/Cm$^2$:
A glass dish with an area of 56.7 cm$^2$ was prepared, and 3.78 g of the solution resulting from step #5 was weighed in it.

The dish thus filled was placed in a thermostatic stove under vacuum at the temperature of 30° C. for 8 hours.

The dish containing the film was then removed and left to cool at room temperature.

The resulting film was collected and placed in an aluminium/polythene sachet. The sachet was then heat-sealed.

Example No. 5—Comparison of Diclofenac Permeation in Two Different Films Through Porcine Ear Skin at 37° C.

Two formulations based on diclofenac sodium salt in Soluplus®-based film (Film A: comparison film) and Soluplus combined with phospholipids (Phospholipon 80H) (Film B: film according to the invention) were prepared for evaluation of the ex vivo permeation test with Franz cells using pig skin.

The two formulations differ in terms of the presence or absence of Phospholipon 80H as active ingredient absorption promoter.

Qualitative/Quantitative Composition of the Two Anhydrous Films:

| Ingredient | Film A (% w/w) | Film B (% w/w) |
|---|---|---|
| Diclofenac sodium | 3.0 | 3.0 |
| Phospholipon 80H | — | 5.0 |
| Propylene glycol | 19.9 | 19.9 |
| Antifoam | 0.1 | 0.1 |
| Soluplus | 77 | 72 |
| | 100.0 | 100.0 |

Film Preparation:
Films A and B were produced with the ingredients and quantities set out in the table below:

| Ingredient | Film A (% w/w) | Film B (% w/w) |
|---|---|---|
| Diclofenac sodium | 0.6 | 0.6 |
| Phospholipon 80H | | 1.0 |
| Propylene glycol | 3.98 | 3.98 |
| Antifoam (30% emulsion) | 0.02 | 0.02 |
| Soluplus | 15.4 | 14.4 |
| Purified water | 79.82 | 79.82 |
| | 100 | 100 |

Preparation of Film A:
Step #1: The diclofenac sodium was dissolved in the specified quantity of water.

Step #2: The Soluplus® was weighed in a glass beaker, and the propylene glycol and antifoam were added. The propylene glycol was left to absorb the Soluplus.

Step #3: The solution obtained in step #1 was added slowly to the mixture obtained in step #2. The resulting mixture was maintained under stirring until the Soluplus had completely dissolved, to give a slightly opalescent solution.

Step #4: 1.960 g of the solution resulting from step #3 was spread on a PVCD film with a circular mould having a radius of 5 cm and an area of 78.5 cm$^2$, and placed in a forced-air stove at the temperature of 60° C. for 45 minutes.

At the end of the drying process the film was extracted from the PVCD support and cooled at room temperature for about 6 hours.

The film formed weighed 5 mg/cm$^2$.

Step #5: The film was packaged in sachets and hermetically sealed.

Preparation of Film B:
Step #1: The diclofenac sodium was dissolved in the specified quantity of water.

Step #2: The Soluplus® was weighed in a glass beaker, and the propylene glycol, Phospholipon 80H and antifoam were added. The propylene glycol was left to absorb the Soluplus, and the mixture was then mixed until the Phospholipon 80H was incorporated in the Soluplus.

Step #3: The solution obtained in step #1 was added slowly to the mixture obtained in step #2. The resulting mixture was maintained under stirring until the Soluplus® was completely dissolved and the Phospholipon 80H dispersed. The resulting mixture was ultrasonicated in an ultrasonic bath to give a homogeneous opalescent microdispersion.

Step #4: 1.960 g of the solution resulting from step #3 was spread on a PVCD film with a circular mould having a radius of 5 cm and an area of 78.5 cm$^{2t}$ and placed in a forced-air stove at the temperature of 60° C. for 45 minutes.

At the end of the drying process the film was extracted from the PVCD support and cooled at room temperature for about 6 hours.

The film formed weighed 5 mg/cm$^2$.

Step #5: The film was packaged in sachets and hermetically sealed.

Permeation Test:
The apparatus used consisted of:
Franz cells (FIG. 1): receptor chamber volume 11 ml; donor compartment diameter 1.5 cm;
Stirring and temperature control system.
Procedure
After the removal of subcutaneous fat, portions of porcine ear skin were thoroughly cleaned with 0.9% saline solution. Before storage at −20° C., the thickness of each disc of skin was determined.

Before each permeability experiment, the tissue samples were thawed at room temperature in saline solution (0.9% w/v of NaCl).

The samples were then mounted in the diffusion cells (exposed area 1.8 cm$^2$) with the stratum corneum facing towards the donor compartment and the dermis facing towards the receptor compartment. The receptor compartment of the cell was filled with the selected medium (0.9% w/v of NaCl). During the experiments, the receptor solution was maintained under stirring at 37° C. A quantity of film corresponding to 15 mg was applied to the surface of the skin/membrane in the donor compartment. 200 µl aliquots were collected from the receptor side at the specified time intervals (0.5, 1, 2, 4 and 6 hours), and immediately replaced with 200 µl of fresh medium solution. The permeated diclofenac concentration was determined by the HPLC-ES-MS/MS method.

HPLC-ES-MS/MS Method

The HPLC System used was the 2690 Alliance System (Waters, Milford, Mass., USA), combined with a QUATTRO-LC triple-quadrupole mass spectrometer (Micromass; Waters) with electrospray (ES) interface. The diclofenac concentration was determined by HPLC-ES-MS/MS under the following experimental conditions:

HPLC column: Waters XSELECT CSH C18 column (5 µm, 150 mm×2.1 mm i.d.).

Figure 2:
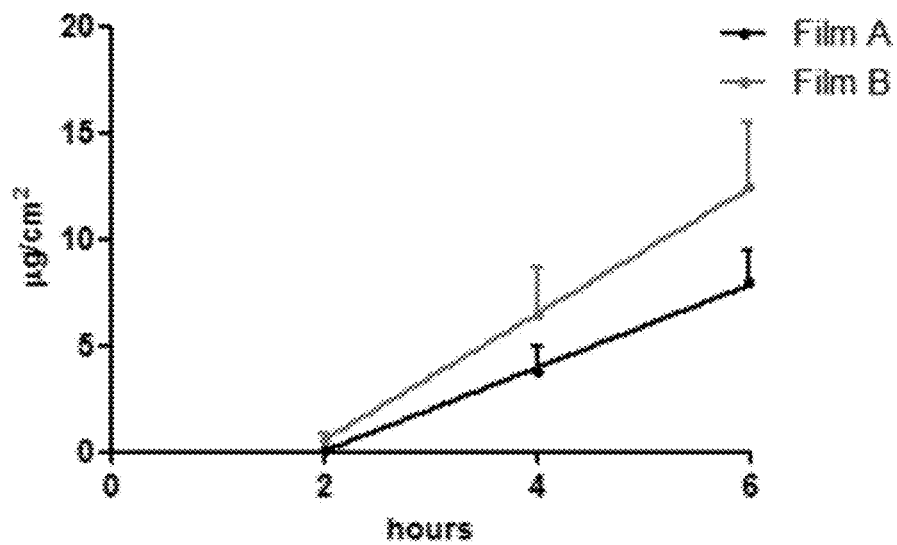
FIG. 2 is a graph showing the permeability profiles at 37° C. of a film A (comparison profile) and a film B (according to the invention) as reported in Example 5.

Composition of mobile phase and elution mode: Solvent A: 15 mM ammonium acetate buffer; Solvent B: Acetonitrile: methanol=75:25 v/v; Isocratic elution Solvent A: Solvent B=40:60 v/v Column temperature: 40° C.
Flow rate: 0.15 ml/min
Injection volume: 10 µL
Linearity range: 0.05-20 µg/mL Under the conditions reported above, the retention time of diclofenac is about 6.1±0.1 min Data Processing and Results The cumulative quantity permeated per surface unit is plotted in the graph vs. time for the two films. The permeability profiles at 37° C. are shown in FIG. 2. The steady-state flux (J, µg cm$^{-2}$ h$^{-1}$) and lag time were estimated by extrapolation from the straight line on the graph. The quantity of diclofenac permeated through the porcine ear skin (expressed as µg/cm$^2$) and steady-state flux J for the two films are shown in the table below. These values are the mean of three independently replicate experiments for each film.

Quantity of diclofenac permeated (µg/cm$^2$) for the two films at 37° C.

| Time | Film A | | Film B | |
| --- | --- | --- | --- | --- |
| (hours) | Mean (n: 3) | SD | Mean (n: 3) | SD |
| 0.5 | n.d. | n.c. | n.d. | n.c. |
| 1 | n.d. | n.c. | n.d. | n.c. |
| 2 | 0.12 | 0.06 | 0.59 | 0.31 |
| 4 | 3.80 | 1.17 | 6.44 | 2.20 |
| 6 | 7.92 | 1.58 | 12.43 | 3.04 |
| J (µg cm$^{-2}$ h$^{-1}$) | 1.95 ± 0.21 | | 2.96 ± 0.41 | | n.d. not detected;
n.c. not calculated

A paired t-test (two tailed) test was conducted to compare the two films. The slopes of the two formulations are significantly different (P<0.05), and the differences between the elevations are significant.

CONCLUSIONS

The permeation of diclofenac through the two membranes was significantly greater for film B according to the invention, while the lag time of the two formulations tested was similar (approximately 2 hours).

The invention claimed is:

1. A fabric for application to the skin comprising a pharmaceutical or cosmetic composition, or a dehydrated form thereof, for topical application to the stratum corneum comprising:
    a) a cosmetically or pharmaceutically active substance;
    b) a polyvinylcaprolactam/polyvinyl acetate/polyethylene glycol copolymer;
    c) a phospholipid, wherein the phospholipid is hydrogenated phosphatidylcholine;
    d) a solvent comprising water or a water-ethanol mixture;
    wherein the active substance and the copolymer are solubilized in the solvent;
    wherein the composition is in the form of a liquid solution; and
    wherein the phospholipid is present in mircrodispersed form;
    wherein the solubilisation of the active substance and the copolymer, and the microdispersion of the phospholipid, are configured to allow penetration of the active substance through the stratum corneum.

2. The fabric according to claim 1 wherein the weight ratio between the polyvinylcaprolactam/polyvinyl acetate/polyethylene glycol copolymer and the phospholipid is 1:1 to 1:1000.

3. The fabric according to claim 2, wherein the pharmaceutically or cosmetically active substance is selected from the group consisting of antarcticine, polyglutamic acid, menthol/menthyl lactate, vanillyl butyl ester, escin, hyaluronic acid sodium salt, silver sulfadiazine, troxerutin and diclofenac sodium.

4. The fabric according to claim 1, wherein the pharmaceutically or cosmetically active substance is selected from the group consisting of antarcticine, polyglutamic acid, menthol/menthyl lactate, vanillyl butyl ester, escin, hyaluronic acid sodium salt, silver sulfadiazine, troxerutin and diclofenac sodium.

5. A method for cosmetic treatment of skin comprising:
    applying an effective amount of a cosmetic composition for topical application to a stratum corneum of the skin comprising:
    a) a cosmetically or pharmaceutically active substance;
    b) a polyvinylcaprolactam/polyvinyl acetate/polyethylene glycol copolymer;
    c) a phospholipid, wherein the phospholipid is hydrogenated phosphatidylcholine;
    d) a solvent comprising water or a water-ethanol mixture;
    wherein the active substance and the copolymer are solubilized in the solvent;
    wherein the composition is in the form of a liquid solution; and
    wherein the phospholipid is present in mircrodispersed form;
    wherein the solubilisation of the active substance and the copolymer, and the microdispersion of the phospholipid, are configured to allow penetration of the active substance through the stratum corneum;
    allowing the active ingredient to penetrate the the stratum corneum into the skin.

* * * * *